United States Patent
Chou (10) Patent No.: US 7,393,638 B2
(45) Date of Patent: *Jul. 1, 2008

(54) ASSAY SYSTEM AND METHODS FOR DETECTING SARS-CV

(75) Inventor: George Chin-Sheng Chou, Hsin (TW)

(73) Assignee: AsiaGEN Corporation, Tainan Hsien (TW)

( * ) Notice: Subject to any disclaimer, the term of this patent is extended or adjusted under 35 U.S.C. 154(b) by 471 days.

This patent is subject to a terminal disclaimer.

(21) Appl. No.: 10/609,604

(22) Filed: Jul. 1, 2003

(65) Prior Publication Data

US 2005/0003340 A1 Jan. 6, 2005

(51) Int. Cl.
*C12Q 1/68* (2006.01)
(52) U.S. Cl. ........................................... 435/6
(58) Field of Classification Search .................. 435/7.1, 435/4, 28, 283.1, 968, 975, 287.21
See application file for complete search history.

(56) References Cited

U.S. PATENT DOCUMENTS

| RE37,891 E | * | 10/2002 | Collins et al. | 435/6 |
| 2001/0019826 A1 | * | 9/2001 | Ammann | 435/6 |
| 2005/0003340 A1 | * | 1/2005 | Chou | 435/5 |
| 2005/0048473 A1 | * | 3/2005 | Arad | 435/5 |

* cited by examiner

*Primary Examiner*—Jon Weber
*Assistant Examiner*—Paul Martin
(74) *Attorney, Agent, or Firm*—Troxell Law Office, PLLC (57) ABSTRACT

The present invention relates to an assay system and methods for detecting SARS coronavirus (SARS-CV) from the samples (especially for urine) of suspected patient in the control of SARS to provide updated information of prognosis as well as the criteria for discharging a recovered patient from a hospital. The present invention also relates to an apparatus for performing the integration of thermal and magnetic control in the same apparatus to largely reduce the time of hybridization less than 20 minutes and the whole process of SARS-CV detection is less than 5 hours.

7 Claims, 4 Drawing Sheets

ASSAY SYSTEM AND METHODS FOR DETECTING SARS-CV

FIELD OF THE INVENTION

The present invention relates to an assay system and methods for detecting SARS coronavirus (SARS-CV) from the samples of suspected patient in the control of SARS. The present invention also relates to an apparatus for performing the integration of thermal and magnetic control in the same apparatus to largely reduce the time of hybridization less than 20 minutes and the whole process of SARS-CV detection is less than 5 hours.

BACKGROUND OF THE INVENTION

Severe acute respiratory syndrome (SARS) is a respiratory illness that has recently been reported in Asia, North America, and Europe. In general, SARS is being noticed with a fever greater than 100.4° F. [>38.0° C.]. Other symptoms may include headache, body aches, and an overall feeling of discomfort. Some people also experience mild respiratory symptoms. After 2 to 7 days, SARS patients may develop a dry cough and have trouble breathing with the symptom of atypical pneumonia.

The primary way that SARS appears to spread is by close person-to-person contact. Most cases of SARS have involved people who cared for or lived with someone with SARS, or had direct contact with infectious material (for example, respiratory secretions, stool and others) from a person who has SARS. Potential ways in which SARS can be spread include touching the skin of other people or objects that are contaminated with infectious droplets and then touching victim's eye(s), nose, or mouth. This can happen when someone who is sick with SARS coughs or sneezes droplets onto themselves, other people, or nearby surfaces. It also is possible that SARS can be spread more broadly through the air or by other ways that are currently not known.

Scientists studying the etiology of SARS have detected a previously unrecognized coronavirus in patients with SARS. The new SARS coronavirus (SARS-CV) is the leading hypothesis for the cause of SARS. Initial diagnostic testing for suspected SARS patients should include chest radiograph, pulse goniometry, blood cultures, sputum Gram's stain and culture, and testing for various viral respiratory pathogens including influenza A and B and respiratory syncytial virus. Clinicians should save any available clinical specimens (respiratory, blood, and serum) for additional testing until a specific diagnosis is made. Acute and convalescent (greater than 21 days after onset of symptoms) serum samples should be collected from each patient who meets the SARS case definition. Paired sera and other clinical specimens should be collected for advanced diagnosis.

According to the expression "Severe Acute Respiratory Syndrome (SARS): Laboratory diagnostic tests" described on 29 Apr. 2003 from WHO website, researchers in several countries are working towards developing fast and accurate laboratory diagnostic tests for the SARS coronavirus (SARS-CV). However, until standardized reagents for virus and antibodies detection are available and methods have been adequately field tested, SARS diagnosis remains based on the clinical and epidemiological findings: acute febrile illness with respiratory symptoms not attributed to another cause and a history of exposure to a suspect or probable case of SARS or their respiratory secretions and other bodily fluids.

According to the Centers for Disease Control and Prevention (CDC), "Initial diagnostic testing for suspected SARS patients should include chest radiograph, pulse oximetry, blood cultures, sputum Gram's stain and culture, and testing for viral respiratory pathogens, notably influenza A and B and respiratory syncytial virus. A specimen for Legionella and pneumococcal urinary antigen testing should also be considered."

In general, there are three current methods for detecting SARS-CV. That is, molecular tests, antibody tests and cell culture.

Although molecular tests such as polymerase chain reaction (PCR) can detect genetic material of the SARS-CV in various specimens (blood, stool, respiratory secretions or body tissues sampling for SARS diagnostic tests), existing PCR tests are very specific but lack sensitivity. This means that negative tests cannot rule out the presence of the SARS virus in patients. Furthermore, contamination of samples in laboratories in the absence of laboratory quality control can lead to false positive results. In addition, negative PCR results do not exclude SARS. SARS-CV PCR can be negative for the following reasons: (1) the patient is not infected with the SARS coronavirus; the illness is due to another infectious agent (virus, bacterium, fungus) or a non-infectious cause; and (2) the test results are incorrect ("false-negative"). Current tests need to be further developed to improve sensitivity. Specimens were not collected at a time when the virus or its genetic material was present. The virus and its genetic material may be present for a brief period only, depending on the type of specimen tested.

Antibody tests detect antibodies produced in response to the SARS coronavirus infection. Different types of antibodies (IgM and IgG) appear and change in level during the course of infection. They can be undetectable at the early stage of infection. IgG usually remains detectable after resolution of the illness. However, the test formats (such as ELISA (Enzyme Linked ImmunoSorbant Assay) and IFA (Immunofluorescence Assay) are being developed. Further, although some patients have detectable coronavirus antibody within 14 days of illness onset, definitive interpretation of negative coronavirus antibody tests is possible only for specimens obtained >21 days after onset of fever.

To monitor the explosive invasiveness of SARS-CV, an early diagnosis of virus itself would be essential to solve the urgency of detection of SARS-CV. Most of time, viral pathogens are able to down-regulate the host immune system that may end up with a low grade or delayed immune response. Therefore, host antibody couldn't be the good surrogate marker for diagnosis.

The presence of the infectious virus can be detected by inoculating suitable cell cultures (e.g., Vero cells) with patient specimens (such as respiratory secretions, blood or stool) and propagating the virus in vitro. Once isolated, the virus must be identified as SARS-CV using further tests. Cell culture is a very demanding test, but currently (with the exception of animal trials) only means to show the existence of a live virus. It has to be performed under at least biosafety safety level (BSL) 3 conditions. Positive cell culture results indicate the presence of live SARS-CV in the sample tested. However, negative cell culture results do not exclude SARS as the similar reason as negative PCR test result.

All tests for SARS-CV available so far have limitations. Extreme caution is therefore necessary when management decisions are to be based on virological test results. In particular, false negative test results (due to low sensitivity, unsuitable sample type, or time of sampling, etc.) may give a false sense of security; in the worst case, they could allow persons carrying the SARS virus, and therefore capable of infecting others, to escape detection.

In addition to allowing the rapid diagnosis of SARS infection, the availability of diagnostic tests will help to address important questions such as the period of virus shedding (and communicability) during convalescence, the presence of virus in different body fluids and excreta, and the presence of virus shedding during the incubation period.

Appropriate specimen should be collected and analyzed upon the timing and severity of disease. Diagnostic samples should be suitable for viral culture, PCR, antigen detection, immunostaining and/or serological antibody assays. In general, blood, sputum, throat swab and stools are frequently studied in case of SARS. For unknown reason, it seldom uses urine to detect or assay SARS-CV.

Given the above, current available assay cannot quickly and completely detect SARS-CV. It requires a quick assay with high specificity and sensitivity to detect SARS-CV from the easily available samples (such as urine).

SUMMARY OF THE INVENTION

The present invention relates to an assay system and methods for detecting SARS-CV from the samples of suspected patient in the control of SARS.

The present invention also relates to an apparatus for performing the dissociation of nucleic acid double strands, hybridization, washing, the separation of magnetic beads and thermal control in the same apparatus.

BRIEF DESCRIPTION OF THE DRAWINGS

FIG. 1 shows SARS cDNA being. specifically amplified and screened by the assay system of the invention.

FIG. 2 shows the screen of clinical specimen from urine and throat swab by the assay system of the invention.

FIG. 3 shows the apparatus of the invention.

FIG. 4 shows that no SARS-CV can be detected from the urine of healthy healthcare employee by the assay system of the invention.

DETAILED DESCRIPTION OF THE INVENTION

When patient infected by SARS-CV, the incubation time may vary from 2 to 10 days. It usually causes fever a few days after the incubation period and cytokine storm will be happening after the on-set of fever. In addition, cytokine storming, Immune-complexes-mediated pathogenesis could be one of the mechanisms that resulted in damaging the oxygen exchange capacity due to the fibrosis of the damaged lung tissue. A similar scenario could be occurred in the basement membrane of Glomerulus in the kidney that may cause the leakage of SARS-CV into urine. This phenomenon could be positively correlated to the severity of disease.

A urinalysis is a common examination of the urine by physical or chemical means. Because urine examination is a non-invasive method, most of patients are happy to use such examination to check their healthy conditions. Thanks to the development of molecular biology and chemistry, urine examination for detecting SARS-CV could be achieved.

Urine sample monitoring for SARS-CV plays significant role in screening massive clinical samples, decreasing the risk of sampling and providing updated information of prognosis as well as the criteria for discharging a recovered patient from a hospital. Information on the amount of infectious virus excreted in the urine by SARS patients is required to assess the risk of transmission of infection by these routes. In particular, false negative test results due to low sensitivity, unsuitable sample type, or time of sampling may give a false sense of security; in the worst case, they could allow persons carrying the SARS virus, and therefore capable of infecting others, to escape detection. To be on the safe side, it requires the further identification to check false negative test results. Given the above, a thorough urine monitoring for SARS-CV is recommended for the control of the pandemic of disease.

The present invention provides a method for detecting SARS coronavirus (SARS-CV) DNA from the samples of suspected patient comprising:

(a) hybridizing the SARS-CV cDNA with SARS-CV-specific probes in hybridization tube wherein the probe linked to magnetic bead;

(b) transferring hybridization tubes to magnetic wells for washing;

(c) adding blocking solution into the tubes;

(d) adding avidin enzyme complex or streptavidin enzyme complex into the tubes (e) performing washing reaction to remove interfering material by the aid of magnetic field;

(f) suspending magnetic beads; and (g) detecting the luminescent or color change after adding substrate of enzyme.

In general, blood, sputum, throat swab and stools are frequently studied in case of SARS. For unknown reason, it seldom uses urine to detect or assay SARS-CV. It could be that the current assays are hard to achieve specificity and sensitivity. Surprisingly, the urine can be easily detected by the use of the system of the invention.

Polymerase Chain Reaction (PCR) PCR is described in Saiki et al. (1985), Science, 230 1350. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target DNA can be amplified a million fold or more in about two to four hours. PCR is a molecular biology tool which must be used in conjunction with a detection technique to determine the results of amplification. In the present invention, biotinylated primer pairs are used in the PCR amplification. That is, forward primer is:GAAGCTATTCGTCACGTTCG and reverse one is biotin-CTGTAGAAAATCCTAGCTGGAG.

As used herein, a "probe" is a substance, e.g., a molecule, that can be specifically recognized by a particular target. Generally, probes will be linked to solid support to facilitate the separation of DNA. In the invention, the probes linked to magnetic beads (MagProbe) are preferred. The sequence of the probe in MagProbe is amine-TAGAGGCTGTCATGCAAT.

Commonly employed labels include, but are not limited to, biotin, fluorescent molecules, radioactive molecules, chromogenic substrates, chemi-luminescence, and the like. The methods for biotinylating nucleic acids are well known in the art, as are methods for introducing fluorescent molecules and radioactive molecules into oligonucleotides and nucleotides.

When biotin is employed, it is detected by avidin, streptavidin or the like, which is conjugated to a detectable marker, such as an enzyme (e.g., horseradish peroxidase). Enzyme conjugates are commercially available from, for example, Vector Laboratories (Burlingame, Calif.). Steptavidin binds with high affinity to biotin, unbound streptavidin is washed away, and the presence of horseradish peroxidase enzyme is then detected using a luminescence-emission substrate in the presence of peroxide and appropriate buffers. The product may be detected using a Berthold Luminometer (Pforzheim, Germany).

Detection methods are well known for fluorescent, radioactive, chemiluminescent, chromogenic labels, as well as other commonly used labels. Briefly, chemiluminescence can be identified and quantitated most directly by their emission wavelengths and intensity.

In the preferred embodiment, the method of the invention can identify other assays for SARS-CV in a patient to provide updated information of prognosis as well as the criteria for discharging a recovered patient from a hospital. To achieve the integration of thermal and magnetic control in one device facilitating the operation, the present invention also provides an apparatus for performing the dissociation of nucleic acid double strands, hybridization, washing, the separation of magnetic beads and thermal control in the same apparatus, comprising:
(a) the means for fitting reaction containers;
(b) the means for controlling the temperature of the containers; and
(c) the means for controlling the magnetic force of the containers,
wherein the means for controlling the temperature of the containers are connected to the means for fitting reaction containers, and the means for controlling the magnetic force of the containers are connected to the means for fitting reaction containers.

In particular, the means for controlling the temperature of the containers to heat the containers to perform the dissociation of nucleic acid double strands according to temperature change. The thermal controllers are easily bought from the device market. Because most of operating procedure after hybridization involves MagProbe, the means for controlling the magnetic force of the containers are integrated with the thermal controller to make the apparatus of the invention. In particular, the means for controlling the magnetic force of the containers perform the magnetic change of magnetic bead to facilitate hybridization, washing and the separation of magnetic beads in the containers.

The present invention also provides an assay system for detecting SARS coronavirus (SARS-CV) DNA from the samples of suspected patient, the system comprising:

(i) a diagnostic kit for detecting amplified SARS coronavirus (SARS-CV) DNA in the presence of hybridization buffer comprising:
  (a) a probe linked to magnetic bead;
  (b) avidin enzyme complex or streptavidin enzyme complex; and
  (c) enzyme substrate;
(ii) an apparatus for performing the dissociation of nucleic acid double strands, hybridization, washing, the separation of magnetic beads and thermal control in the same apparatus, comprising:
  (a) the means for fitting reaction containers;
  (b) the means for controlling the temperature of the containers; and
  (c) the means for controlling the magnetic force of the containers,
  wherein the means for controlling the temperature of the containers are connected to the means for fitting reaction containers, and the means for controlling the magnetic force of the containers are connected to the means for fitting reaction containers;
(iii) a magnetic rack to bind the magnetic bead on the wall of the containers; and
(iv) a detector.

In the assay system of the invention, the kit further comprises hybridization buffer, washing buffer and blocking buffer. These buffers are easily purchased from commercial products such as those of Pierce, Biolab, Qiagen etc.

In the preferred embodiment, the assay system of the invention can identify other assays for SARS-CV in a patient to provide updated information of prognosis as well as the criteria for discharging a recovered patient from a hospital. In general, the assay system of the invention can reduce the time of hybridization less than 20 minutes and the whole process of SARS-CV detection less than 5 hours.

EXAMPLES

The examples below are non-limiting and are merely representative of various aspects and features of the present invention.

Material and Methods

Major Kit:
1. SARS MagProbe (450 μl, stored in 4° C.)

Oligo-Nucleotides Used:
I). The specific sequence of Biotinylated primer pair used:
1. Forward primer: GAAGCTATTCGTCACGTTCG
2. Reverse primer: Biotin-CTGTAGAAAATCCTAGCTGGAG II). The specific sequence of MagProbe:
Amine-TAGAGGGCTGTCATGCAACT
2. Hybridization Buffer (4.5 ml)
3. Wash Buffer (60 ml)
4. Hybridization tubes (12×75 mm, 25 tubes)
5. Amplification buffer (3 ml, stored in −20° C.)

Detection Kit:
1. Blocking buffer (0.5%, 60 ml stored in 4° C.)
2. SA-HRP (1 mg/ml, 15 μl, stored in −20° C.)
3. HRP substrate A: PierceProd#1856193 (7.5 ml, stored in 4° C.)
4. HRP substrate B: PierceProd#1856194 (7.5 ml, stored in 4° C.)

Other Material and Equipments:
1. Qiagen mini RNA kit
2. Random hexamer
3. dNTP, 200 mM
4. RNasin
5. Sodium pyrophosphate, 20 mM
6. AMV reverse transcriptase
7. DEPC treated water
8. Taq DNA polymerase
9. Phosphate buffer solution (PBS), pH7.0
10. 0.1% PBST (PBS with 0.1% tween-20)
11. 0.5% PBST (PBS with 0.5% tween-20)
12. Magnetic Rack
13. Magnetic Dry Bath
14. Berthol Luminometer Procedures:

I. Viral RNA Isolation
1. PREPARING BUFFERS:
1). EQUILIBRATE BUFFER AVE TO RT FOR ELUTION
2). PREPARE BUFFER AW1, BUFFER AW2, AND CARRIER RNA ACCORDING TO THE INSTRUCTIONS (QIAGENE, USA)
3). Re-dissolve precipitate in Buffer AVL/Carrier RNA by heating, if necessary, and cool to RT before use 4). All centrifugation steps are carried out in RT.
2. Collect specimen of throat swab or urine from patients.
3. Squeeze throat swab in Eppendorf tube containing 150 μl of PBS.
4. Transfer 560 μl of prepared Buffer AVL containing Carrier RNA into 1.5 ml microcentrifuge tube.
5. Transfer 140 μl samples prepared in Step 3 or 140 μl urine samples to the microcentrifuge tube of Step 4. Mix by pulse-vortexing for 15 sec.
6. Incubate at RT for 15 min to ensure a complete inactivation of viral particles.
7. If the sample was kept at frozen state, stay at 70° C. for 10 min. Briefly centrifuge the 1.5 ml microcentrifuge tube to remove drops from the inside of the lid.
8. Add 560 μl of ethanol (96–100%) to the tube, and mix by pulse-vortexing for 15 sec. After mixing, briefly centrifuge the 1.5 ml microcentrifuge tube to remove drops from inside the lid.
9. Carefully apply 630 μl of the solution from Step 8 to the QIAAMP (QIAamp™, a nucleic acid isolator purchased from QIAGEN) spin column (in a 2 ml collection tube) without wetting the rim. Close the cap, and centrifuge at 8,000 rpm for 1 min. Place the QIAAMP spin column into a clean 2 ml collection tube, and discard the tube containing the filtrate.
10. Carefully open the QIAAMP spin column, and repeat step 9.
11. Carefully open the QIAAMP spin column, and add 500 μl of Buffer AW1. Close the cap, and centrifuge at 8,000 rpm for 1 min. Place the QIAAMP spin column in a clean 2 ml collection tube, and discard the tube containing the filtrate.
12. Carefully open the QIAAMP spin column, and add 500 μl of BufferAW2. Close the cap and centrifuge at full speed for 3 min.
13. Place the QIAAMP spin column in a clean 1.5 ml microcentrifuge tube. Discard the old collection tube containing the filtrate.
14. Carefully open the QIAAMP spin column and add 60 μl of Buffer AVE (RT).
15. Close the cap, and incubate at RT for 1 min.
16. Centrifuge at 8,000 rpm for 1 min.

(Viral RNA will be 90% eluted for one AVE elution and it is stable for up to one year when stored at −70° C.)

II. First-Strand CDNA Synthesis for PCR

To prepare the first-strand cDNA, add 1 μl of Random hexamer (10 pmol/μl) to a micro-tube containing 9 μl of viral RNA as the following instructions:
1. 70° C., 5 min
2. Chill on ice for 5 min
3. Centrifuge briefly.
4. Add following components in order:

| | |
|---|---|
| AMV 5X buffer | 5.0 μl |
| 10 mM dNTP mix | 2.5 μl |
| RNasin 40 unit/μl | 1.0 μl |
| Sodium pyrophosphate, 20 mM (Pre-warmed to 42° C.) | 2.5 μl |
| AMV RT | 30 units |

Add DEPC treated $ddH_2O$ to final volume of 25 μl.

5. Mix gently.
6. 37° C., 60 min for random primer
7. 95° C. for 10 min
8. Spin briefly.
9. Place it on ice immediately.
(Note: 2 μl first-strand CDNA products are sufficient for subsequent PCR amplification.)

III. Target Amplification 1. 47.6 μl amplification buffer+0.4 μl Taq DNA polymerase+2 μl sample cDNA
2. Amplification program

| | Temperature | Time | Number of cycles |
|---|---|---|---|
| 1 | 94° C. | 5 min | 1 cycle |
| 2 | 94° C. | 30 sec | 36 cycles |
| | 55.8° C. | 30 sec | |
| | 72° C. | 30 sec | |
| 3 | 72° C. | 10 min | 1 cycle |
| 4 | 4° C. | Stay | — |

IV. Hybridization

1. After labeling hybridization tube, mix 75 μl of $ddH_2O$, 15 μl of MagProbe, 150 μl of hybridization buffer and 50 μl of labeled sample DNA.
2. Keep hybridization tubes at 100° C. dry bath for 5 min.
3. Adjust to 50° C. and keep for 20 min. (100° C. to 50° C. will take about 14 min)
4. Transfer hybridization tubes to magnetic wells and keep for 5 min.
5. Remove hybridization buffer by suction.
6. Add 0.9 ml of pre-heated 50° C. wash buffer to each tube, vortex and put tubes back to magnetic wells and keep for 5 min.
7. Remove hybridization buffer by suction.
8. Repeat Step 6–7, put hybridization tubes into test tube rack.

V. Detection
1. In RT, add 200 μl of blocking solution into each tube, vortex and sit for 3 min.
2. Add 5 μl of freshly prepared SA-HRP (99 μl 0.1% PBST+1 μl SA-HRP stock), vortex and disperse evenly. Sit at RT for 40 min.
3. Put hybridization tubes into magnetic rack and sit for 5 min. Then remove solution by suction.
4. Add 0.9 ml of 0.5% PBST, vortex and put tubes back to magnetic rack. Sit for 5 min then remove solution by suction. Repeat once.
5. Add 25 μl of PBS to each tube to re-suspend magnetic beads by vortexing.
6. Add 50 μl of mixed HRP substrate to each tube (25 μl HRP substrate A+25 μl HRP substrate B)
7. Detect the relative luminescent unit (RLU) of each sample by Luminometer.

Example 1

SARS cDNA (SARS-1 and SARS-2) were PCR-amplified and proofreading by MagProbe specified for an oligonucleotide sequence that is inside the amplified fragment, F1R1. FIG. 1 clearly indicates that there is no noise from negative controls, both *M. tuberculosis* genomic DNA and $ddH_2O$.

Example 2

Clinical specimen from urine and throat swab were assayed by the assay system of the invention. As indicated in FIG. 2, 40% urine samples collected at various timing were identified to be SARS-CV positive and 80% of swab samples from one of the same patient were SARS-CV positive.

Example 3

Figure 1:
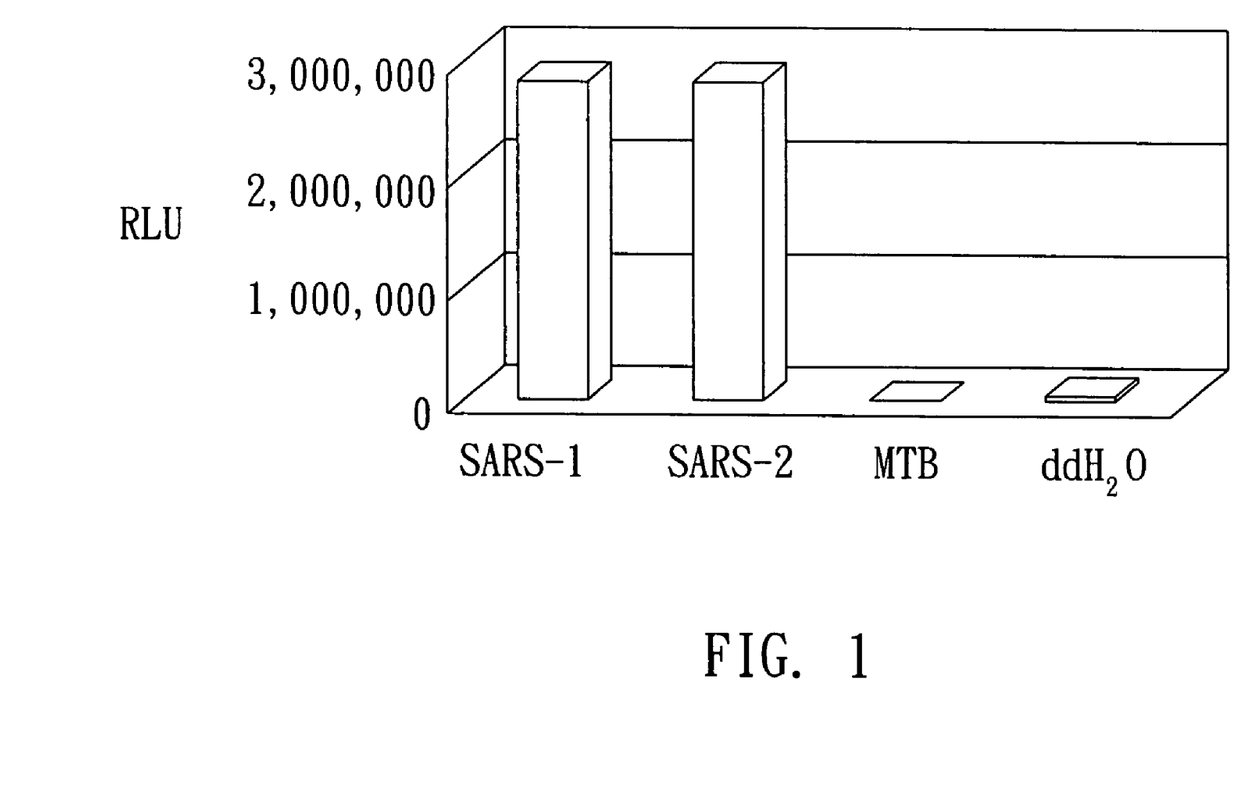
Figure 2:
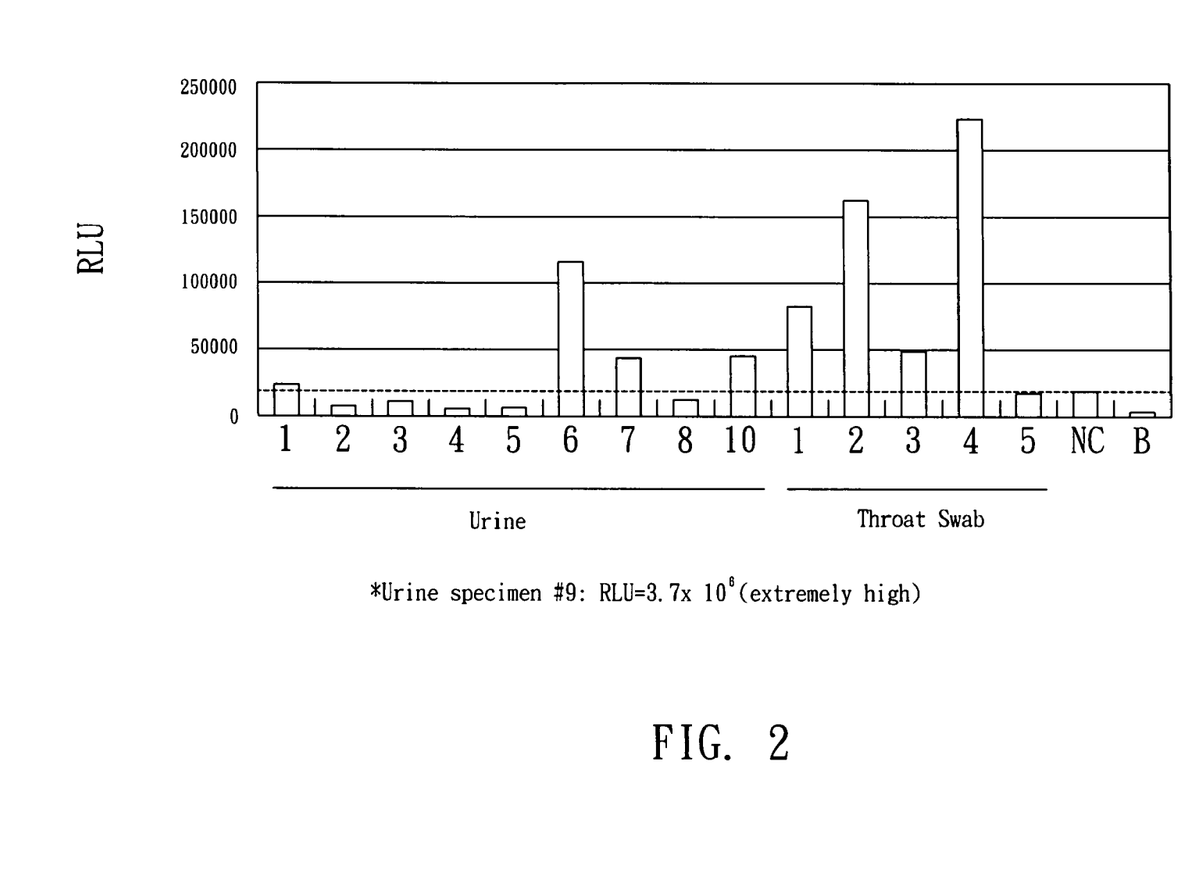
Figure 3:
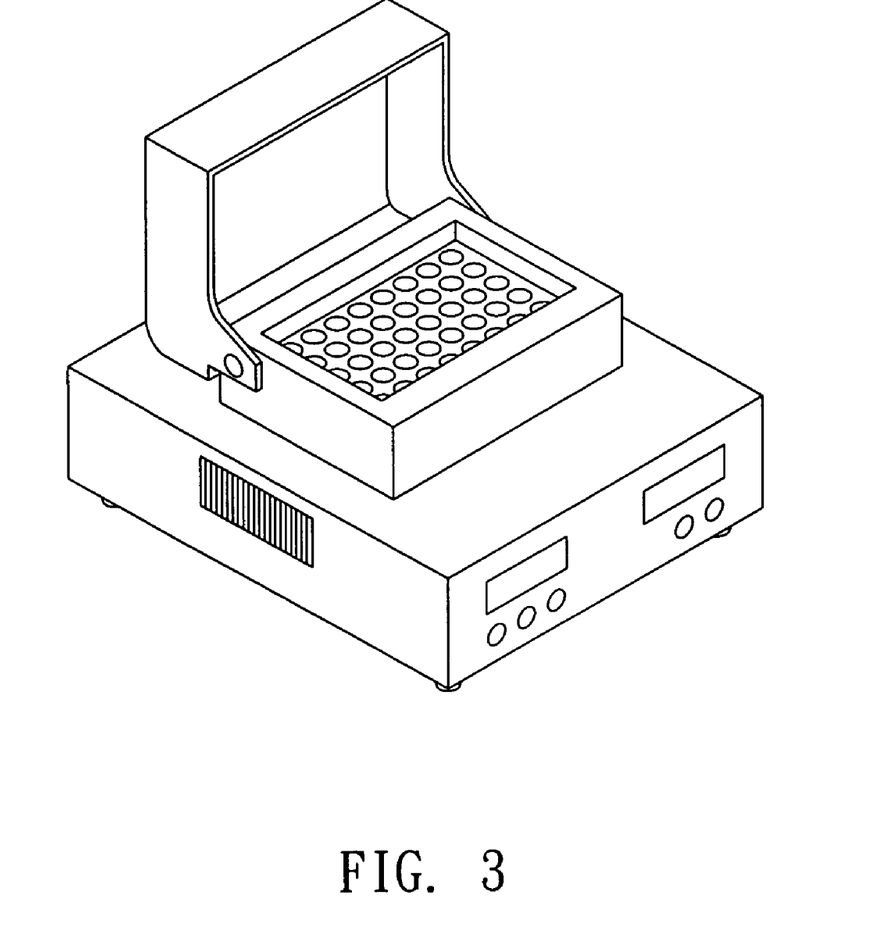
Figure 4:
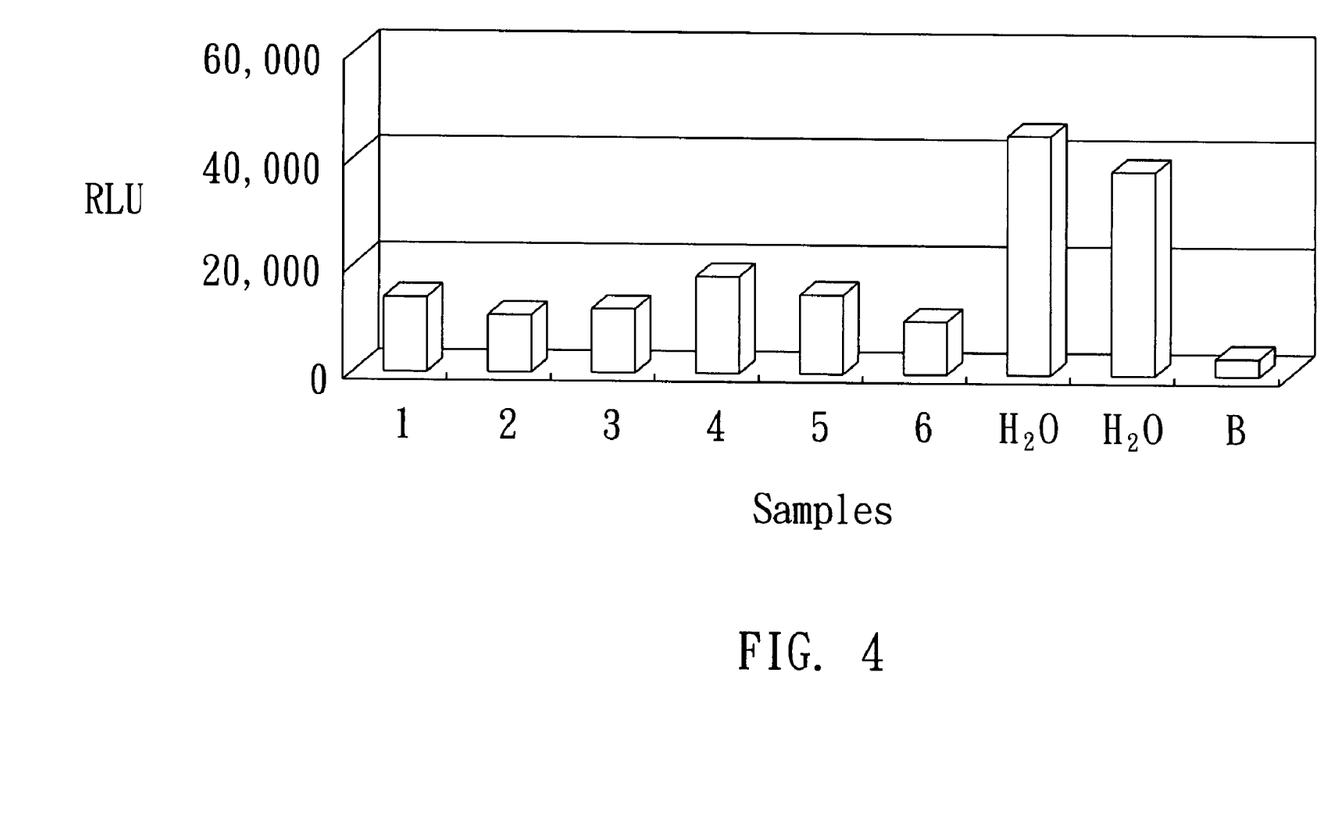

Clinical specimen from urine of healthy healthcare employee were assayed by the assay system of the invention. It was clearly indicated in FIG. 4 that there are no SARS-CV can be detected from the urine of healthy healthcare employee.

Discussions

Eradication of SARS-CV from human community may not be achieved unless a solid strategy of vaccination is timely and completely carried out. Therefore, dependable diagnoses have to be strictly enforced from time to time. Among so many different diagnostics, direct detection of infected viruses would be the first line of choice, i.e. a molecular device that can directly detect viral genome should be applied. In the other hand, sample analysis is also a key to uncover the infection that may precisely detect the virus, delineate the severity and the prognosis of the disease. To detect SARS-CV from suspected patient urine is just one of the good example that can identify SARS-CV, decrease the risk of sampling, describe the severity and evaluate the prognosis of disease. Especially, a urinary SARS-CV negative report is a must for discharging a recovered patient from healthcare unit, when the etiology of SARS is not yet fully understood. It will be significant to detect urine samples for quarantine or routine monitoring of a massive cohesive community. As shown in Examples 1–3, the assay system and method of the invention have been demonstrated that they have very high specificity and sensitivity for SARS-CV from urine. Furthermore, the apparatus of integrating thermal and magnetic means of the invention and MagProbe are convenient for the operator to reduce the time of hybridization less than 20 minutes and the whole process of SARS-CV detection less than 5 hours.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. An assay system for detecting SARS (severe acute respiratory syndrome) coronavirus (SARS-CV) DNA from a sample of a suspected patient, the system comprising:
   (i) a diagnostic kit for detecting biotinylated SARS coronavirus (SARS-CV) DNA, which is amplified in advance by biotinylated primers, in the presence of hybridization buffer, said kit comprising:
      (a) a probe consisting of the sequence amine-TAGAGGGCTGTCATGCAACT (SEQ ID NO: 3) linked to a magnetic bead;
      (b) avidin enzyme complex or streptavidin enzyme complex; and
      (c) substrate for said enzyme;
   (ii) an apparatus for performing the dissociation of nucleic acid double strands, hybridization, washing, the separation of magnetic beads and thermal control in the same apparatus, comprising:
      (a) a means for fitting reaction containers;
      (b) a means for controlling the temperature of the containers; and
      (c) a means for controlling the magnetic force of the containers, wherein the means for controlling the temperature of the containers are connected to the means for fitting reaction containers, and the means for controlling the magnetic force of the containers are connected to the means for fitting reaction containers;
   (iii) a magnetic rack to bind the magnetic beads on the wall of the containers; and
   (iv) a detector for the reaction of the substrate with the enzyme.

2. The assay system of claim 1, wherein the streptavidin enzyme complex in the kit is streptavidin horseradish peroxidase (SA-HRP).

3. The assay system of claim 1, wherein the kit further comprises hybridization buffer, washing buffer and blocking buffer.

4. The assay system of claim 1, wherein the detector is luminometer or spectrophotometer.

5. The assay system of claim 1, further comprising an additional test selected from the group consisting of a molecular test, an antibody test, and a cell culture, wherein the additional test is capable of detecting SARS-CV.

6. The assay system of claim 1 which reduces the time of hybridization to less than 20 minutes and the whole process of SARS-CV detection to less than 5 hours.

7. An assay system for detecting SARS (severe acute respiratory syndrome) coronavirus (SARS-CV) DNA from a sample of a suspected patient, the system comprising:
   (i) a diagnostic kit for detecting biotinylated SARS coronavirus (SARS-CV) DNA, which is amplified in advance by biotinylated primers, in the presence of hybridization buffer, said kit comprising:
      (a) a probe consisting of the sequence amine-TAGAGGGCTGTCATGCAACT (SEQ ID NO: 3) linked to a magnetic bead;
      (b) avidin enzyme complex or streptavidin enzyme complex; and
      (c) substrate for said enzyme;
   (ii) an apparatus for performing the dissociation of nucleic acid double strands, hybridization, washing, the separation of magnetic beads and thermal control in the same apparatus, comprising:
      (a) a means for fitting reaction containers;
      (b) a means for controlling the temperature of the containers; and
      (c) a means for controlling the magnetic force of the containers, wherein the means for controlling the temperature of the containers are connected to the means for fitting reaction containers, and the means for controlling the magnetic force of the containers are connected to the means for fitting reaction containers;
   (iii) a magnetic rack to bind the magnetic beads on the wall of the containers;
   (iv) a detector for the reaction of the substrate with the enzyme, and
   (v) an additional test selected from the group consisting of: a molecular test, an antibody test, and a cell culture, wherein the additional test is capable of detecting SARS-CV.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagctattc gtcacgttcg                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```

```
ctgtagaaaa tcctagctgg ag                                              22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tagagggctg tcatgcaact                                                 20
```